US012622635B2

(12) United States Patent
Been et al.

(10) Patent No.: US 12,622,635 B2
(45) Date of Patent: May 12, 2026

(54) DISPLAY DEVICE AND METHOD OF MEASURING SKIN MOISTURE USING THE SAME

(71) Applicant: Samsung Display Co., Ltd., Yongin-si (KR)

(72) Inventors: Kyounghun Been, Asan-si (KR); Jinwoo Kim, Hwaseong-si (KR); Byeongkyu Jeon, Busan (KR)

(73) Assignee: Samsung Display Co., Ltd., Yongin-si (KR)

( * ) Notice: Subject to any disclaimer, the term of this patent is extended or adjusted under 35 U.S.C. 154(b) by 1039 days.

(21) Appl. No.: 17/739,145

(22) Filed: May 8, 2022

(65) Prior Publication Data

US 2023/0042134 A1 Feb. 9, 2023

(30) Foreign Application Priority Data

Aug. 5, 2021 (KR) ........................ 10-2021-0102965

(51) Int. Cl.
*A61B 5/00* (2006.01)
*G01N 27/22* (2006.01)
(52) U.S. Cl.
CPC ............ *A61B 5/443* (2013.01); *A61B 5/6898* (2013.01); *G01N 27/223* (2013.01)
(58) Field of Classification Search
None
See application file for complete search history.

(56) References Cited

U.S. PATENT DOCUMENTS 7,402,135 B2 7/2008 Leveque et al.
11,171,185 B2 11/2021 Kim et al.
(Continued)

FOREIGN PATENT DOCUMENTS

KR 10-0938403 1/2010
KR 10-1619081 5/2016
(Continued)

OTHER PUBLICATIONS

Comparative study of five instruments measuring stratum corneum hydration (Comeometer CM 820 and CM 825, Skicon 200, Nova DPM 9003, DermaLab). Part I. In vitro.

*Primary Examiner* — Eric J Messersmith
*Assistant Examiner* — Matthew Eric Ogles
(74) *Attorney, Agent, or Firm* — Womble Bond Dickinson (US) LLP

(57) ABSTRACT
A method of measuring skin moisture includes: measuring, in response to a touch on a touch panel, a first capacitance for a touch area in association with driving first and second electrodes of the touch panel in a mutual sensing mode; measuring, in response to the touch, a second capacitance for the touch area in association with driving one electrode of the first and second electrodes in a self-sensing mode; comparing the first capacitance with a first reference capacitance; determining, in response to the first capacitance being greater than the first reference capacitance, a skin moisture level using the first capacitance and the second capacitance; comparing, in response to the first capacitance being less than the first reference capacitance, the second capacitance with a second reference capacitance; and compensating, in response to the second capacitance being greater than the second reference capacitance, the first capacitance using the second capacitance.

13 Claims, 16 Drawing Sheets

(56)  References Cited

U.S. PATENT DOCUMENTS

| | | | |
|---|---|---|---|
| 11,543,908 B1 * | 1/2023 | Healy | G01R 27/2605 |
| 2012/0062509 A1 * | 3/2012 | Hsu | G06F 3/0446 |
| | | | 345/174 |
| 2015/0293624 A1 * | 10/2015 | Chen | G06F 3/041 |
| | | | 345/174 |
| 2016/0274726 A1 * | 9/2016 | Chung | G06F 3/014 |
| 2018/0276443 A1 * | 9/2018 | Strohmann | G06V 40/1394 |
| 2019/0056823 A1 * | 2/2019 | Stevenson | G06F 3/0443 |
| 2019/0114019 A1 * | 4/2019 | Maguire | G06F 3/041662 |

FOREIGN PATENT DOCUMENTS

| | | |
|---|---|---|
| KR | 10-2009070 | 8/2019 |
| KR | 10-2021-0018702 | 2/2021 |

* cited by examiner

FIG. 9

DISPLAY DEVICE AND METHOD OF MEASURING SKIN MOISTURE USING THE SAME

CROSS-REFERENCE TO RELATED APPLICATIONS

This application claims priority to and the benefit of Korean Patent Application No. 10-2021-0102965, filed Aug. 5, 2021, which is hereby incorporated by reference for all purposes as if fully set forth herein.

BACKGROUND

Field

One or more embodiments generally relate to a display device and a method for measuring skin moisture using the same.

Discussion

A display device provides information to a user by displaying various images on a display screen. In general, the display device may display information within an allocated screen. As the display device is applied to various electronic devices, there is a need for display devices having various functions. For example, a skin moisture meter capable of measuring human skin moisture is of interest. However, because a touch sensor has a measurement area larger than a skin moisture meter, a mutual capacitance value of a center portion of a touch area is lowered in a low ground mass (LGM) state, and thus, the accuracy of skin moisture level measurement may also be reduced.

The above information disclosed in this section is only for understanding the background of the inventive concepts, and, therefore, may contain information that does not form prior art.

SUMMARY

One or more embodiments provide a display device capable of measuring a skin moisture level regardless of an LGM state.

One or more embodiments provide a method of measuring a skin moisture level regardless of an LGM state via a display device.

One or more embodiments provide an apparatus capable of measuring a skin moisture level regardless of an LGM state.

Additional aspects will be set forth in the detailed description which follows, and, in part, will be apparent from the disclosure, or may be learned by practice of the inventive concepts.

According to an embodiment, method of measuring skin moisture includes: measuring, in response to a touch on a touch panel, a first capacitance for a touch area in association with driving a first electrode and a second electrode of the touch panel in a mutual sensing mode; measuring, in response to the touch on the touch panel, a second capacitance for the touch area in association with driving one electrode of the first electrode and the second electrode in a self-sensing mode; comparing the first capacitance with a first reference capacitance; determining, in response to the first capacitance being greater than the first reference capacitance, a skin moisture level using the first capacitance and the second capacitance; comparing, in response to the first capacitance being less than the first reference capacitance, the second capacitance with a second reference capacitance; compensating, in response to the second capacitance being greater than the second reference capacitance, the first capacitance using the second capacitance.

According to an embodiment, a display device includes a display panel, a touch panel, a control module, a comparison part, a computation part, and a moisture calculation part. The touch panel is disposed on the display panel. The control module is configured to: drive the touch panel in each of a mutual sensing mode and a self-sensing mode; measure a first capacitance of a touch area of the touch panel in the mutual sensing mode; and measure a second capacitance of the touch area in the self-sensing mode. The comparison part is configured to: receive the first capacitance and the second capacitance; and compare the first capacitance and the second capacitance with a first reference capacitance and a second reference capacitance, respectively. The computation part is configured to compensate for the first capacitance in response to the first capacitance being less than the first reference capacitance and the second capacitance being greater than the second reference capacitance. The moisture calculation part is configured to determine a skin moisture level using the compensated first capacitance. The computation part is configured to compensate for a value of the first capacitance using a value of the second capacitance.

The foregoing general description and the following detailed description are illustrative and explanatory and are intended to provide further explanation of the claimed subject matter.

BRIEF DESCRIPTION OF THE DRAWINGS

The accompanying drawings, which are included to provide a further understanding of the inventive concepts, and are incorporated in and constitute a part of this specification, illustrate embodiments of the inventive concepts, and, together with the description, serve to explain principles of the inventive concepts.

FIG. 9 is a block diagram illustrating a connection relationship between the moisture measurement part shown in FIG. 8 and a configuration around the moisture measurement part according to an embodiment.

DETAILED DESCRIPTION OF SOME EMBODIMENTS

Figure 1:
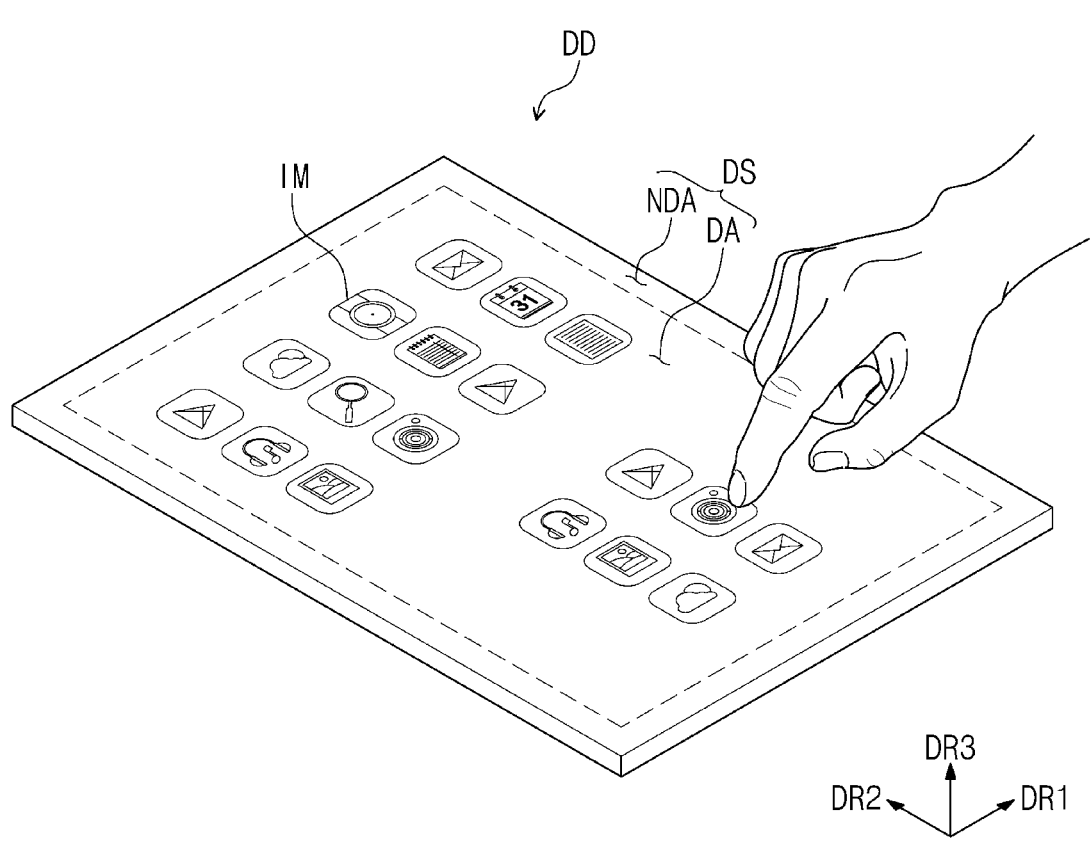
FIG. 1 is a perspective view of a display device according to an embodiment.

In the following description, for the purposes of explanation, numerous specific details are set forth in order to provide a thorough understanding of various embodiments. As used herein, the terms "embodiments" and "implementations" may be used interchangeably and are non-limiting examples employing one or more of the inventive concepts disclosed herein. It is apparent, however, that various embodiments may be practiced without these specific details or with one or more equivalent arrangements. In other instances, well-known structures and devices are shown in block diagram form to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing example features of varying detail of some embodiments. Therefore, unless otherwise specified, the features, components, modules, layers, films, panels, regions, aspects, etc. (hereinafter individually or collectively referred to as an "element" or "elements"), of the various illustrations may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. As such, the sizes and relative sizes of the respective elements are not necessarily limited to the sizes and relative sizes shown in the drawings. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element, it may be directly on, connected to, or coupled to the other element or intervening elements may be present. When, however, an element is referred to as being "directly on," "directly connected to," or "directly coupled to" another element, there are no intervening elements present. Other terms and/or phrases used to describe a relationship between elements should be interpreted in a like fashion, e.g., "between" versus "directly between," "adjacent" versus "directly adjacent," "on" versus "directly on," etc. Further, the term "connected" may refer to physical, electrical, and/or fluid connection. In addition, the DR1-axis, the DR2-axis, and the DR3-axis are not limited to three axes of a rectangular coordinate system, and may be interpreted in a broader sense. For example, the DR1-axis, the DR2-axis, and the DR3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one element's relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing some embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional views, isometric views, perspective views, plan views, and/or exploded illustrations that are schematic illustrations of idealized embodiments and/or intermediate structures. As such, variations from the shapes of the illustrations as a result of, for example, manufacturing techniques and/or tolerances, are to be expected. Thus, embodiments disclosed herein should not be construed as limited to the particular illustrated shapes of regions, but are to include deviations in shapes that result from, for instance, manufacturing. To this end, regions illustrated in the drawings may be schematic in nature and shapes of these regions may not reflect the actual shapes of regions of a device, and, as such, are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

As customary in the field, some embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some embodiments may be physically separated into two or more interacting and discrete blocks, units, and/or modules without departing from the inventive concepts. Further, the blocks, units, and/or modules of some embodiments may be physically combined into more complex blocks, units, and/or modules without departing from the inventive concepts.

Hereinafter, various embodiments will be explained in detail with reference to the accompanying drawings.

FIG. 1 is a perspective view of a display device according to an embodiment.

A display device DD may have a shape of a rectangle having a short side in a first direction DR1 and a long side in a second direction DR2 intersecting the first direction DR1. However, embodiments are not limited thereto. For instance, the display device DD may have various shapes, such as a circle or a polygon.

Hereinafter, a direction substantially perpendicular to a plane defined by the first direction DR1 and the second direction DR2 is defined as a third direction DR3. Furthermore, in the specification, the meaning of "when viewed from above a plane" may mean "when viewed in the third direction DR3".

A top surface of the display device DD may be defined as a display surface DS, and may have a plane defined by the first direction DR1 and the second direction DR2. An image IM generated by the display device DD may be provided to a user through (or via) the display surface DS.

The display surface DS may include a display area DA and a non-display area NDA around the display area DA. The display area DA may display an image, and the non-display area NDA may not display an image. The non-display area NDA may surround the display area DA and may define a border of the display device DD printed in a predetermined color.

The display device DD may be used for a large electronic device, such as a television, a monitor, an outer billboard, or the like. Moreover, the display device DD may be used for small and medium electronic devices, such as a personal computer, a notebook computer, a personal digital terminal, an automotive navigation system, a game console, a smartphone, a tablet, a camera, or the like. However, the above examples are provided only as some embodiments, and the display device DD may be applied to any other electronic device(s) without departing from the inventive concepts.

Figure 2:
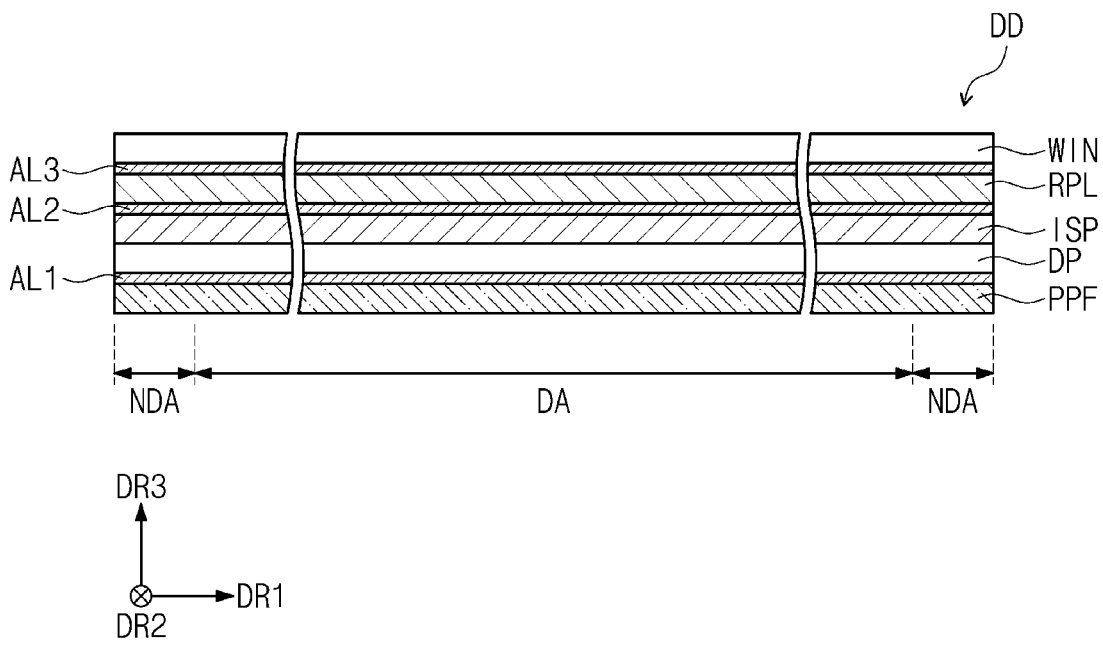
FIG. 2 is a diagram illustrating a cross-section of the display device shown in FIG. 1 according to an embodiment.

FIG. 2 is a diagram illustrating a cross-section of the display device shown in FIG. 1 according to an embodiment. For instance, FIG. 2 illustrates a cross-section of the display device DD when viewed in the first direction DR1.

Referring to FIG. 2, the display device DD may include a display panel DP, an input sensing part ISP, an anti-reflection layer RPL, a window WIN, a panel protection film PPF, and first to third adhesive layers AL1 to AL3.

The display panel DP may be a flexible display panel. The display panel DP according to an embodiment may be a light emitting display panel, but is not limited thereto. For example, the display panel DP may be an organic light emitting display panel or a quantum dot light emitting display panel. A light emitting layer of the organic light emitting display panel may include an organic light emitting material. An emission layer of the quantum dot light emitting display panel may include a quantum dot, a quantum rod, and/or the like. Hereinafter, it is described that the display panel DP is an organic light emitting display panel.

The input sensing part ISP may be disposed on the display panel DP. The input sensing part ISP may include a plurality of sensors for sensing an external input in a capacitive scheme.

The anti-reflection layer RPL may be disposed on the input sensing part ISP. The anti-reflection layer RPL may reduce the reflectance of external light incident from the top surface of the display device DD toward the display panel DP. The anti-reflection layer RPL may include a retarder and a polarizer.

The window WIN may be disposed on the anti-reflection layer RPL. The window WIN may protect the display panel DP, the input sensing part ISP, and the anti-reflection layer RPL from external scratches and impacts.

The panel protection film PPF may be disposed under the display panel DP. The panel protection film PPF may protect a bottom surface of the display panel DP. The panel protection film PPF may include a flexible plastic material, such as polyethylene terephthalate (PET).

The first adhesive layer AL1 may be interposed between the display panel DP and the panel protection film PPF. The display panel DP and the panel protection film PPF may be coupled to each other by the first adhesive layer AL1.

The second adhesive layer AL2 may be interposed between the anti-reflection layer RPL and the input sensing part ISP. The anti-reflection layer RPL and the input sensing part ISP may be coupled to each other by the second adhesive layer AL2.

The third adhesive layer AL3 may be interposed between the window WIN and the anti-reflection layer RPL. The window WIN and the anti-reflection layer RPL may be coupled to each other by the third adhesive layer AL3.

Figure 3:
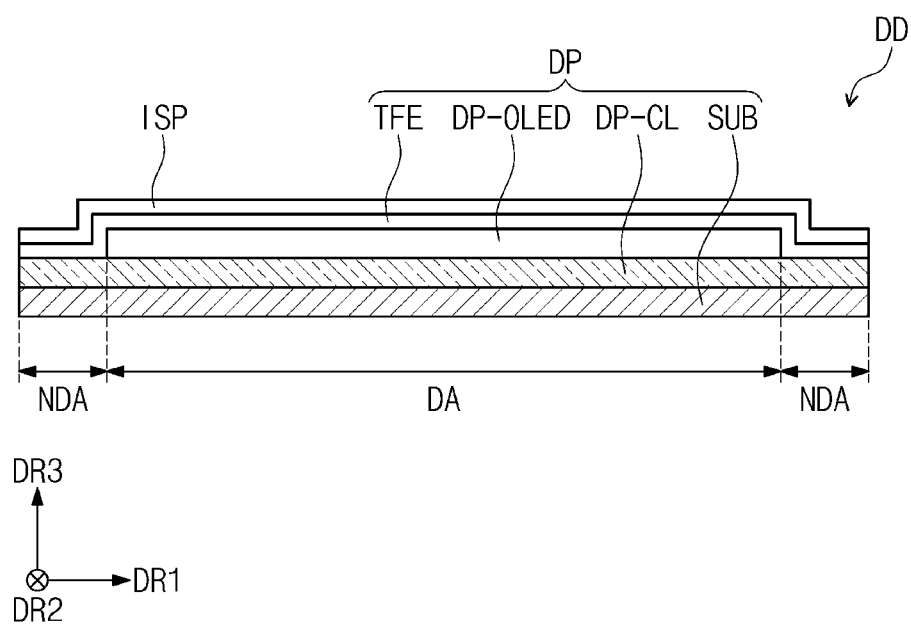
FIG. 3 is a cross-sectional view of the display panel shown in FIG. 2 according to an embodiment.

FIG. 3 is a cross-sectional view of the display panel shown in FIG. 2 according to an embodiment.

Referring to FIG. 3, the display panel DP may include a substrate SUB, a circuit element layer DP-CL disposed on the substrate SUB, a display element layer DP-OLED disposed on the circuit element layer DP-CL, and an encapsulation layer TFE disposed on the display element layer DP-OLED.

The substrate SUB may include the display area DA and the non-display area NDA around the display area DA. The substrate SUB may include a flexible plastic material. For example, the substrate SUB may include polyimide (PI).

The circuit element layer DP-CL may be disposed on the substrate SUB. The circuit element layer DP-CL may include an insulating layer, a semiconductor pattern, a conductive pattern, a signal line, and the like. The insulating layer, the semiconductor layer, and the conductive layer may be formed on the substrate SUB in a manner, such as coating, evaporation, and/or the like. Afterward, the insulating layer, the semiconductor layer, and the conductive layer may be selectively patterned by performing a photolithography process a plurality of times. Afterward, the semiconductor pattern, the conductive pattern, and the signal line included in the circuit element layer DP-CL may be formed.

The display element layer DP-OLED may be disposed on the display area DA. The display element layer DP-OLED may include a light emitting element. For example, the display element layer DP-OLED may include an organic light emitting material, a quantum dot, a quantum rod, a micro-light emitting diode (LED), and/or a nano-LED.

The encapsulation layer TFE may be disposed on the circuit element layer DP-CL so as to cover the display element layer DP-OLED. The encapsulation layer TFE may protect the display element layer DP-OLED from foreign objects, such as moisture, oxygen, and dust particles.

The input sensing part ISP may be disposed on the display panel DP. The input sensing part ISP may detect an external input applied from the outside. The external input may be a user input. The user input may include various types of external inputs, such as a portion of the user's body, light, heat, pens, pressure, and/or the like.

The input sensing part ISP may be formed on the display panel DP through sequential processes. In this case, it may be expressed that the input sensing part ISP is directly disposed on the display panel DP. The expression "being directly disposed" may mean that a third component is not interposed between the input sensing part ISP and the display panel DP. That is, a separate adhesive member may not be interposed between the input sensing part ISP and the display panel DP. Alternatively, the input sensing part ISP may be coupled to the display panel DP through an adhesive member. The adhesive member may include a common adhesive or a common sticking agent.

In some embodiments, the display device DD may further include an optical layer disposed on the input sensing part ISP. The optical layer may improve the front luminance of the display device DD by controlling a direction of light incident from the display panel DP.

Figure 4:
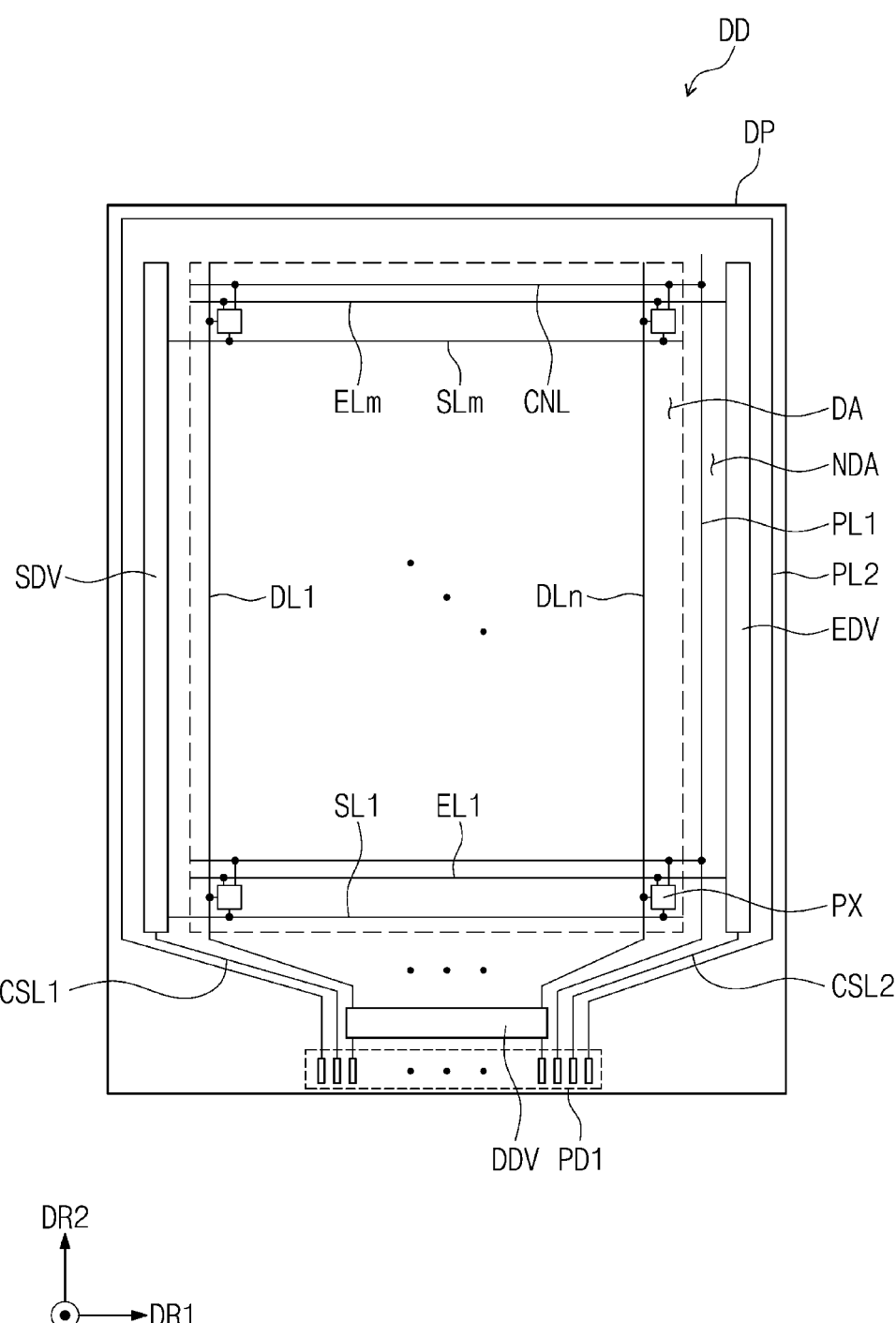
FIG. 4 is a plan view of the display panel shown in FIG. 2 according to an embodiment.

FIG. 4 is a plan view of the display panel shown in FIG. 2 according to an embodiment.

Referring to FIG. 4, the display device DD may include the display panel DP, a scan driver SDV, a data driver DDV, an emission driver EDV, and a plurality of first pads PD1.

The display panel DP may have a rectangular shape having long sides extending in the second direction DR2 and short sides extending in the first direction DR1. However, the shape of the display panel DP is not limited thereto. The display panel DP may include the display area DA and the non-display area NDA surrounding the display area DA.

The display panel DP may include a plurality of pixels PX, a plurality of scan lines SL1 to SLm, a plurality of data lines DL1 to DLn, a plurality of emission lines EL1 to ELm, first and second control lines (CSL1, CSL2), first and second power supply lines (PL1, PL2), and connecting lines CNL. Each of "m" and "n" are natural numbers.

The pixels PX may be positioned in the display area DA. The scan driver SDV and the emission driver EDV may be disposed in the non-display area NDA adjacent to the long sides of the display panel DP, respectively. The data driver DDV may be disposed in the non-display area NDA adjacent to one of the short sides of the display panel DP. When viewed from above a plane, the data driver DDV may be adjacent to a bottom end of the display panel DP.

The scan lines SL1 to SLm may extend in the first direction DR1 so as to be connected to the pixels PX and the scan driver SDV. The data lines DL1 to DLn may extend in the second direction DR2 so as to be connected to the pixels PX and the data driver DDV. The emission lines EL1 to ELm may be extended in the first direction DR1 so as to be connected to pixels PX and the emission driver EDV.

The first power supply line PL1 may extend in the second direction DR2 and may be disposed in the non-display area NDA. The first power supply line PL1 may be interposed between the display area DA and the emission driver EDV, but is not limited thereto. For example, the first power supply line PL1 may be interposed between the display area DA and the scan driver SDV.

The connecting lines CNL may extend in the first direction DR1 and may be arranged in the second direction DR2. The connecting lines CNL may be connected to the first power supply line PL1 and the pixels PX. The first voltage may be applied to the pixels PX through the first power supply line PL1 and the connecting lines CNL that are connected to each other.

The second power supply line PL2 may be disposed in the non-display area NDA. The second power supply line PL2 may extend along the long sides of the display panel DP and the other short side of the display panel DP at which the data driver DDV is not disposed. The second power supply line PL2 may be disposed outside the scan driver SDV and the emission driver EDV.

In some embodiments, the second power supply line PL2 may extend toward the display area DA so as to be connected to the pixels PX. A second voltage having a level lower than a first voltage may be applied to the pixels PX through the second power supply line PL2.

The first control line CSL1 may be connected to the scan driver SDV and may extend toward the bottom end of the display panel DP when viewed from above a plane. The second control line CSL2 may be connected to the emission driver EDV and may extend toward the bottom end of the display panel DP when viewed from above a plane. The data driver DDV may be interposed between the first control line CSL1 and the second control line CSL2.

The first pads PD1 may be disposed on the display panel DP. The first pads PD1 may be closer to the bottom end of the display panel DP than the data driver DDV. The data driver DDV, the first power supply line PL1, the second power supply line PL2, the first control line CSL1, and the second control line CSL2 may be respectively connected to the first pads PD1. The data lines DL1 to DLn may be connected to the data driver DDV. The data driver DDV may be connected to the first pads PD1 corresponding to the data lines DL1 to DLn.

In some embodiments, the display device DD may further include a timing controller for controlling operations of the scan driver SDV, the data driver DDV, and the emission driver EDV, and a voltage generator for generating first and second voltages. The timing controller and the voltage generator may be connected to corresponding first pads PD1 through a printed circuit board.

The scan driver SDV may generate a plurality of scan signals. The scan signals may be applied to the pixels PX through the scan lines SL1 to SLm. The data driver DDV may generate a plurality of data voltages. The data voltages may be applied to the pixels PX through the data lines DL1 to DLn. The emission driver EDV may generate a plurality of emission signals. The emission signals may be applied to the pixels PX through the emission lines EL1 to ELm.

The pixels PX may receive the data voltages in response to scan signals. The pixels PX may display images by emitting light of luminance corresponding to data voltages in response to the emission signals. The emission time of the pixels PX may be controlled by the emission signals.

Figure 5:
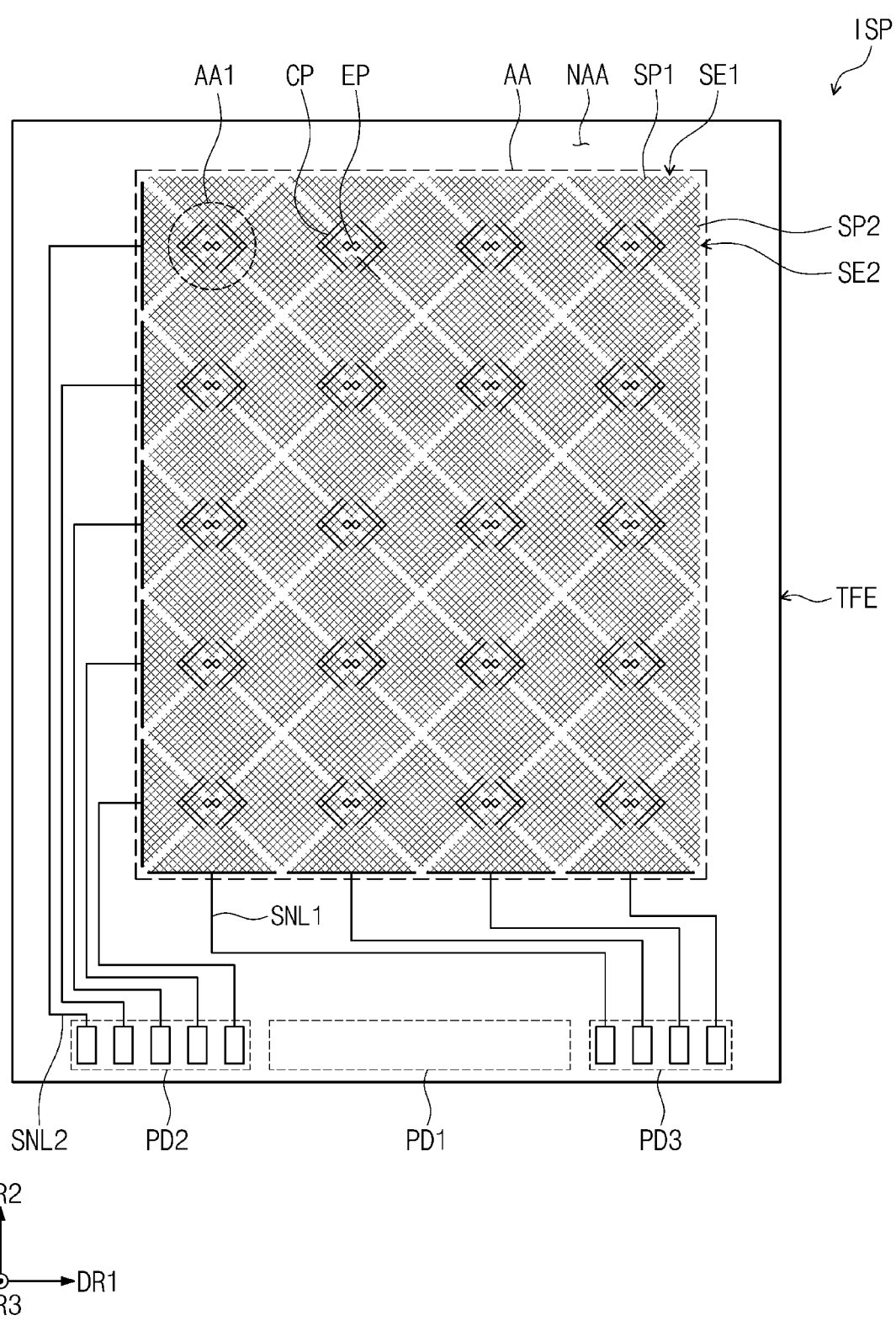
FIG. 5 is a plan view of the input sensor shown in FIG. 2 according to an embodiment.

FIG. 5 is a plan view of the input sensor shown in FIG. 2 according to an embodiment.

Referring to FIG. 5, the input sensing part ISP may include a plurality of sensing electrodes SE1, SE2, a plurality of sensing lines SNL1, SNL2, a plurality of second pads PD2, and a plurality of third pads PD3. The sensing electrodes SE1, SE2, the sensing lines SNL1, SNL2, the second pads PD2, and the third pads PD3 may be disposed on the thin film encapsulation layer TFE.

The planar area of the input sensing part ISP may include an active area AA and an inactive area NAA around the active area AA. The active area AA may overlap the display area DA. The inactive area NAA may overlap the non-display area NDA. The sensing electrodes SE1, SE2 may be disposed in the active area AA. The second pads PD2 and the third pads PD3 may be disposed in the inactive area NAA.

The sensing lines SNL1, SNL2 may be connected to ends of the sensing electrodes SE1, SE2 and may extend to the inactive area NAA so as to be connected to the second pads PD2 and the third pads PD3.

The sensing electrodes SE1, SE2 may include the plurality of first sensing electrodes SE1 extending in the second direction DR2 and arranged in the first direction DR1, and the plurality of second sensing electrodes SE2 extending in the first direction DR1 and arranged in the second direction DR2. The second sensing electrodes SE2 may extend such that the second sensing electrodes SE2 are insulated from the first sensing electrodes SE1 and intersect with the first sensing electrodes SE1.

The sensing lines SNL1, SNL2 may include the plurality of first sensing lines SNL1 connected to the first sensing electrodes SE1 and the plurality of second sensing lines SNL2 connected to the second sensing electrodes SE2. The first sensing lines SNL1 may be connected to the third pads PD3. The second sensing lines SNL2 may be connected to the second pads PD2.

The first sensing electrodes SE1 may be defined as driving electrodes, and the second sensing electrodes SE2 may be defined as sensing electrodes. The input sensing part ISP may be driven in a mutual sensing mode or self-sensing mode. A sensing controller may provide driving signals to the input sensing part ISP and may receive sensing signals from the input sensing part ISP.

Each of the first sensing electrodes SE1 may include a plurality of first sensors SP1 arranged in the second direction DR2 and a plurality of connecting patterns CP connecting the first sensors SP1. Each of the connecting patterns CP is interposed between two first sensors SP1, which are adjacent to each other in the second direction DR2, so as to connect the two first sensors SP1.

Each of the second sensing electrodes SE2 may include a plurality of second sensors SP2 arranged in the first direction DR1 and a plurality of extension patterns EP extending from the second sensors SP2. Each of the extension patterns EP is arranged between two second sensors SP2, which are adjacent to each other in the first direction DR1, so as to extend from the two second sensors SP2.

The first sensors SP1 and the second sensors SP2 may have a mesh shape. The first sensors SP1 and the second sensors SP2 may not overlap each other and may be spaced from each other, and may be alternately arranged with each other. Capacitances may be formed by the first sensors SP1 and the second sensors SP2. The extension patterns EP may not overlap the connecting patterns CP.

The first and second sensors SP1, SP2 and the extension patterns EP may be disposed on the same layer. The connection patterns CP may be positioned on a layer different from the first and second sensors SP1, SP2 and the extension patterns EP.

Figure 6:
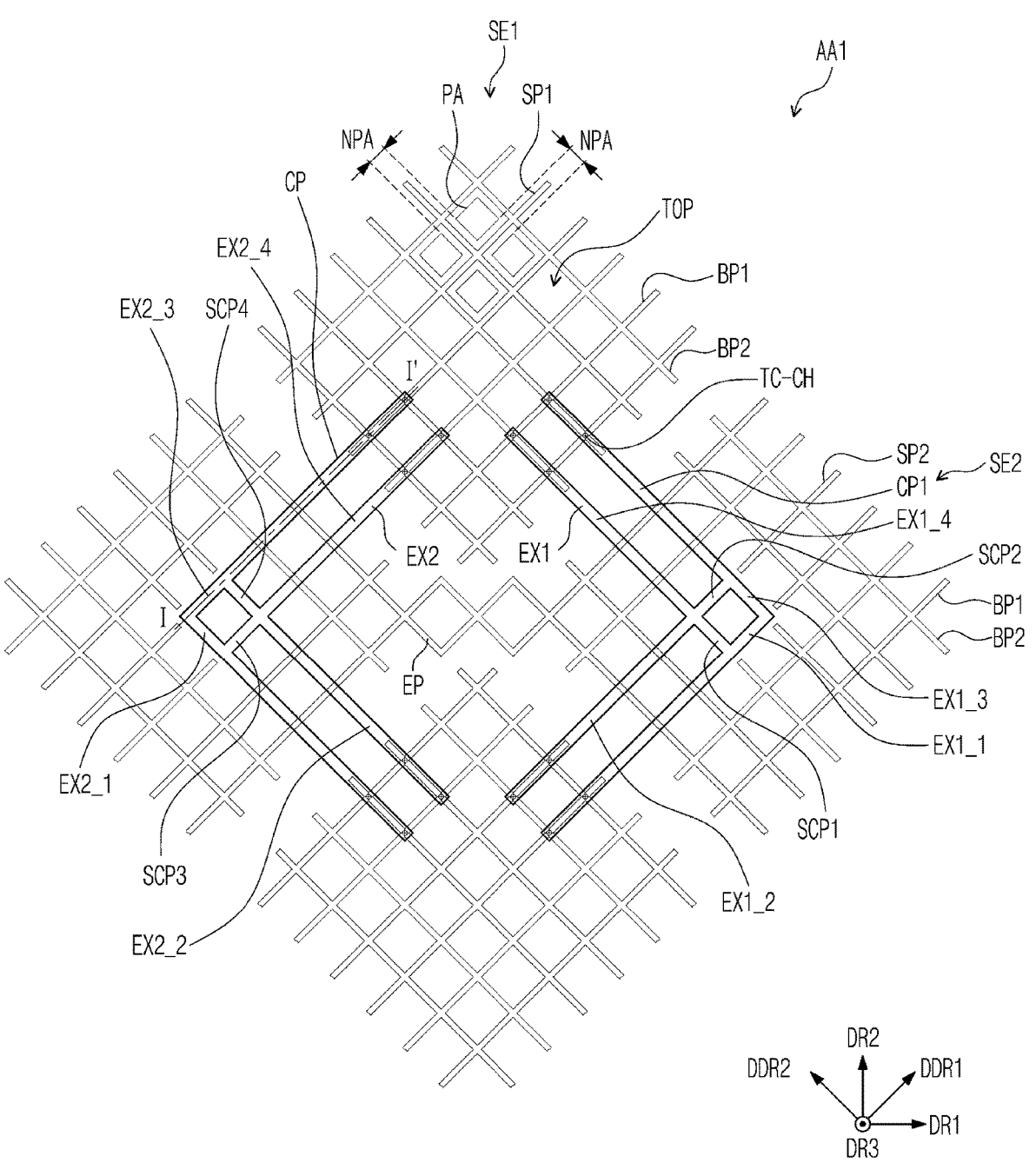
FIG. 6 is an enlarged view of portion AA1 illustrated in FIG. 5 according to an embodiment.

FIG. 6 is an enlarged view of portion AA1 illustrated in FIG. 5 according to an embodiment.

Referring to FIG. 6, to have a mesh shape, each of the first and second sensors SP1, SP2 may include a plurality of first branch parts BP1 extending in a first diagonal direction DDR1, and a plurality of second branch parts BP2 extending in a second diagonal direction DDR2.

The first diagonal direction DDR1 may be defined as a direction intersecting with the first and second directions DR1, DR2 on a plane defined by the first and second directions DR1, DR2. The second diagonal direction DDR2 may be defined as a direction intersecting with the first diagonal direction DDR1 on a plane defined by the first and second directions DR1, DR2.

First branch parts BP1 and second branch parts BP2 of the first and second sensors SP1, SP2 may intersect with each other and may be integrally formed with each other. Rhombus-shaped touch openings TOP may be defined by the first branch parts BP1 and the second branch parts BP2.

When viewed from above a plane, emission areas PA may be disposed in the touch openings TOP. Four emission areas PA disposed in the one first sensor SP1 are illustrated as an example; however, a plurality of emission areas PA may be substantially disposed in the touch openings TOP.

The emission areas PA may have a rhombus shape. However, the shape of the emission areas PA is not limited thereto. The first branch parts BP1 and the second branch parts BP2 may overlap each other in a non-emission area NPA.

The connecting pattern CP may extend such that the connecting pattern CP does not overlap the extension pattern EP, and thus, the connecting pattern CP may connect the first sensors SP1. The connecting pattern CP may be connected to the first sensors SP1 through a plurality of contact holes TC-CH. The connecting pattern CP may extend toward the first sensors SP1 via the second sensors SP2.

The extension pattern EP may be interposed between the first sensors SP1 and may extend from the second sensors SP2. The second sensors SP2 and the extension pattern EP may be integrated with each other. The extension pattern EP may have a mesh shape. The extension pattern EP, the first sensors SP1, and the second sensors SP2 may be simultaneously patterned and formed with the same material.

The connecting pattern CP may include a first extension part EX1 and a second extension part EX2 having a shape symmetrical to that of the first extension part EX1. The extension pattern EP may be interposed between the first extension part EX1 and the second extension part EX2. The first extension part EX1 may extend via an area overlapping one second sensor of the second sensors SP2 and may be connected to the first sensors SP1. The second extension part EX2 may extend via an area overlapping another second sensor of the second sensors SP2 and may be connected to the first sensors SP1.

Hereinafter, the first sensors SP1 are defined as a first upper sensor SP1 and a first lower sensor SP1 depending on a relative placement location. The second sensors SP2 are defined as a second left sensor SP2 and a second right sensor SP2 depending on a relative placement location.

Figure 7:
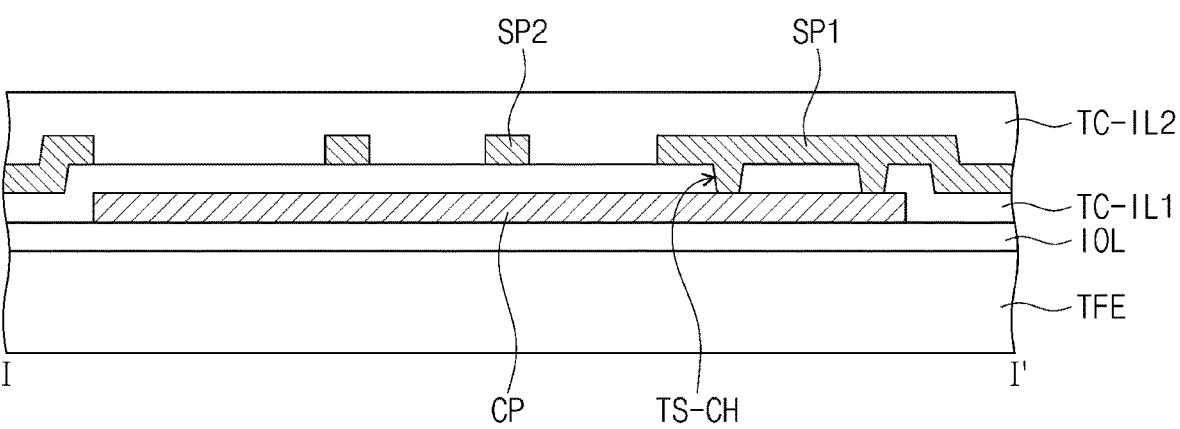
FIG. 7 is a cross-sectional view taken along sectional line I-I' shown in FIG. 6 according to an embodiment.

Portions of the first and second extension parts EX1 and EX2 adjacent to sides of the first and second extension parts EX1 and EX2 may be connected to the first lower sensor SP1 through contact holes TC-CH. Portions of the first and second extension parts EX1 and EX2 adjacent to the other sides of the first and second extension parts EX1 and EX2 may be connected to the first upper sensor SP1 through contact holes TC-CH. The structure of the contact holes TC-CH are illustrated in FIG. 7.

The first extension part EX1 may include a first sub extension part EX1_1 and a second sub extension part EX1_2, which extend in the first diagonal direction DDR1, a third sub extension part EX1_3 and a fourth sub extension part EX1_4, which extend in the second diagonal direction DDR2, a first sub conductive pattern SCP1 extending in the second diagonal direction DDR2, and a second sub conductive pattern SCP2 extending in the first diagonal direction DDR1.

Portions of the first and second sub extension parts EX1_1, EX1_2 adjacent to sides of the first and second sub extension parts EX1_1, EX1_2 may be connected to the first lower sensor SP1 through contact holes TC-CH. Portions of the third and fourth sub extension parts EX1_3, EX1_4 adjacent to sides of the third and fourth sub extension parts EX1_3, EX1_4 may be connected to the first upper sensor SP1 through contact holes TC-CH.

The other side of the first sub extension part EX1_1 may extend from the other side of the third sub extension part EX1_3. The other side of the second sub extension part EX1_2 may extend from the other side of the fourth sub extension part EX1_4. The first sub conductive pattern SCP1 may extend in the second diagonal direction DDR2 from the other side of the fourth sub extension part EX1_4, and may extend to the first sub extension part EX1_1. The second sub conductive pattern SCP2 may extend in the first diagonal direction DDR1 from the other side of the second sub extension part EX1_2, and may extend to the third sub extension part EX1_3.

The first sub extension part EX1_1, the second sub extension part EX1_2, the third sub extension part EX1_3, the fourth sub extension part EX1_4, the first sub conductive pattern SCP1, and the second sub conductive pattern SCP2 may be integrated with one another.

The first and second sub extension parts EX1_1, EX1_2 may extend to intersect with a predetermined number of the second branch parts BP2, which are adjacent to the first lower sensor SP1, from among the second branch parts BP2 of the second right sensor SP2. The first branch parts BP1 of the second right sensor SP2 may not be disposed in some areas overlapping the first and second sub extension parts EX1_1, EX1_2 and the second sub conductive pattern SCP2.

The third and fourth sub extension parts EX1_3, EX1_4 may extend to intersect with a predetermined number of the first branch parts BP1, which are adjacent to the first upper sensor SP1, from among the first branch parts BP1 of the second right sensor SP2. The second branch parts BP2 of the second right sensor SP2 may not be disposed in some areas overlapping the third and fourth sub extension parts EX1_3, EX1_4 and the first sub conductive pattern SCP1.

The second extension part EX2 may include a fifth sub extension part EX2_1 and a sixth sub extension part EX2_2, which extend in the second diagonal direction DDR2, a seventh sub extension part EX2_3 and an eighth sub extension part EX2_4, which extend in the first diagonal direction DDR1, a third sub conductive pattern SCP3 extending in the first diagonal direction DDR1, and a fourth sub conductive pattern SCP4 extending in the second diagonal direction DDR2.

The second left sensor SP2 may have a structure symmetrical to that of the second right sensor SP2. The second extension part EX2 may have a structure symmetrical to that of the first extension part EX1. Accordingly, hereinafter, descriptions of the fifth to eighth sub extension parts EX2_1 to EX2_4 and third and fourth sub conductive patterns SCP3, SCP4 will be omitted to avoid redundancy.

FIG. 7 is a cross-sectional view taken along sectional line I-I' shown in FIG. 6 according to an embodiment.

Referring to FIG. 7, an insulating layer IOL may be disposed on the thin film encapsulation layer TFE. The insulating layer IOL may be an inorganic layer. The connecting pattern CP may be disposed on the insulating layer IOL. A first insulating layer TC-IL1 may be disposed on the connecting pattern CP and the insulating layer IOL. The first insulating layer TC-IL1 may be an inorganic layer or an organic layer.

The first sensors SP1 and the second sensors SP2 may be disposed on the first insulating layer TC-IL1. The extension pattern EP integrated with the second sensors SP2 may also be disposed on the first insulating layer TC-IL1.

The connecting pattern CP may be connected to the first sensors SP1 through the contact holes TC-CH defined in the first insulating layer TC-IL1. A second insulating layer TC-IL2 may be disposed on the first insulating layer TC-IL1 so as to cover the first sensors SP1 and the second sensors SP2. The second insulating layer TC-IL2 may be an organic layer.

Figure 8:
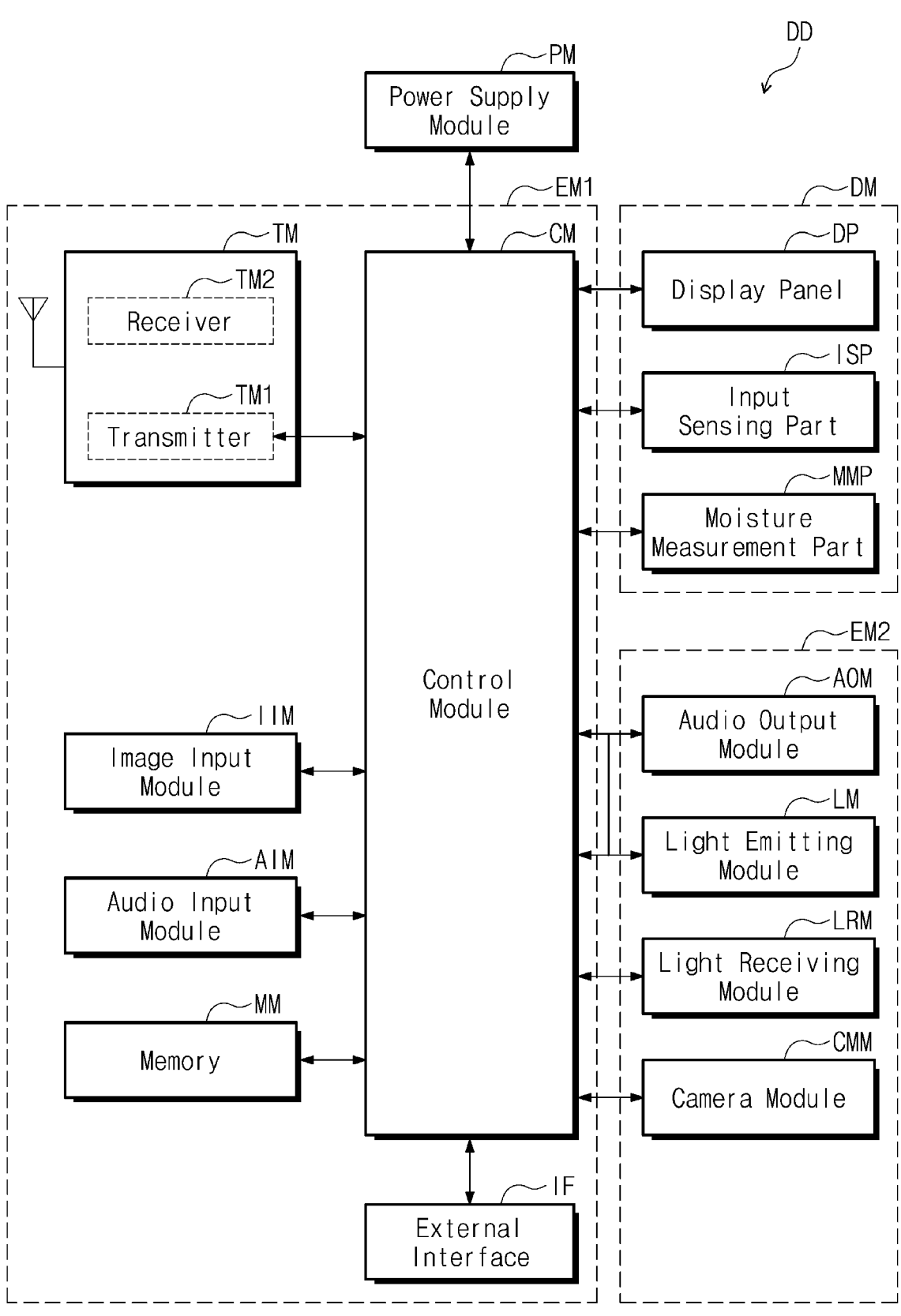
FIG. 8 is a block diagram of the display device shown in FIG. 1 according to an embodiment.

FIG. 8 is a block diagram of the display device shown in FIG. 1 according to an embodiment.

Referring to FIG. 8, the display device DD according to an embodiment may include the display module DM, a power supply module PM, a first electronic module EM1, and a second electronic module EM2. The display module DM, the power supply module PM, the first electronic module EM1, and the second electronic module EM2 may be electrically connected to one another.

The power supply module PM may supply power for overall operations of the display device DD. The power supply module PM may include a general battery module.

Each of the first electronic module EM1 and the second electronic module EM2 may include various functional modules for operating the display device DD. The first electronic module EM1 may be directly mounted on a motherboard electrically connected to the display module DM or may be mounted on a separate board so as to be electrically connected to the motherboard through a connector.

The first electronic module EM1 may include a control module CM, a wireless communication module TM, an image input module IIM, an audio input module AIM, a memory MM, and an external interface IF. Some of the modules may be electrically connected to the motherboard through a flexible circuit board without being mounted on the motherboard.

The control module CM may control overall operations of the display device DD. The control module CM may activate or deactivate the display module DM. The control module CM may control other modules such as the image input module IIM, the audio input module AIM, or the like based on a touch signal received from the display module DM. Besides, the control module CM may implement a user authentication mode by using fingerprint information received from the display module DM.

The wireless communication module TM may transmit/ receive wireless signals with another terminal using, for instance, Bluetooth and/or Wi-Fi. The wireless communication module TM may transmit/receive voice signals using general communication lines. The wireless communication module TM may include a transmitter TM1, which modulates and transmits a transmission signal, and a receiver TM2 that demodulates a reception signal.

The image input module IIM may convert an image signal into image data to be displayed on the display module DM by processing the image signal. The audio input module AIM receives an external sound signal from a microphone in a recording mode, a speech recognition mode, or the like, and then may convert the external sound signal into electrical voice data.

The external interface IF may operate as an interface that connects to an external charger, a wired/wireless data port, a card socket (e.g., a memory card, a SIM/UIM card, or the like), and/or the like.

The second electronic module EM2 may include an audio output module AOM, a light emitting module LM, a light receiving module LRM, and a camera module CMM. The configurations may be mounted directly on a motherboard, may be mounted on a separate board so as to be electrically connected to the display module DM through a connector, or may be electrically connected to the first electronic module EM1.

The audio output module AOM may convert audio data received from the wireless communication module TM or audio data stored in the memory MM and then may output the converted data to the outside. The light emitting module LM may generate and output light. The light emitting module LM may output infrared light. The light emitting module LM may include an LED element. The light receiving module LRM may detect the infrared light. When the infrared light having a predetermined level or more is detected, the light receiving module LRM may be activated. The light receiving module LRM may include a complementary metal-oxide-semiconductor (CMOS) sensor.

After the infrared light being generated by the light emitting module LM is output, the infrared light may be reflected by an external object (e.g., a user's finger or face), and then the reflected infrared light may be incident on the light receiving module LRM. The camera module CMM may capture an external image.

The display module DM may include the display panel DP, the input sensing part ISP, and a moisture measurement part MMP. The display panel DP may display an image using image data provided from the control module CM. The control module CM may drive the display module DM in an initial mode and a main mode following the initial mode. For instance, the display panel DP may be driven in the initial mode and the main mode under the control of the control module CM, and then the display panel DP may display an image corresponding to the initial mode and an image corresponding to the main mode.

The control module CM may drive the input sensing part ISP in a mutual sensing mode and/or a self-sensing mode. In the mutual sensing mode and the self-sensing mode, when the user's skin contacts the input sensing part ISP, the control module CM may measure a capacitance generated by the contacted skin. The control module CM may transmit the measured capacitance to the moisture measurement part MMP. The moisture level of the user's skin may be measured by the moisture measurement part MMP.

The input sensing part ISP may sense an external input (e.g., the user's skin, a touch pen, or the like). The sensed signal may be transmitted to the control module CM as an input signal. The control module CM may control an operation of the display panel DP in response to the input signal. In response to the user's skin contacting the display panel DP, the input sensing part ISP may provide the capacitance generated by the contact of the skin to the control module CM.

The moisture measurement part MMP may determine (e.g., calculate) the moisture level of the user's skin. The moisture measurement part MMP may determine the moisture level of the user's skin by comparing the capacitance provided from the control module CM with a lookup table.

The control module CM may receive the moisture level of the contacted skin and then may drive the display panel DP such that the display panel DP displays the moisture level of the user's skin.

Figure 9:
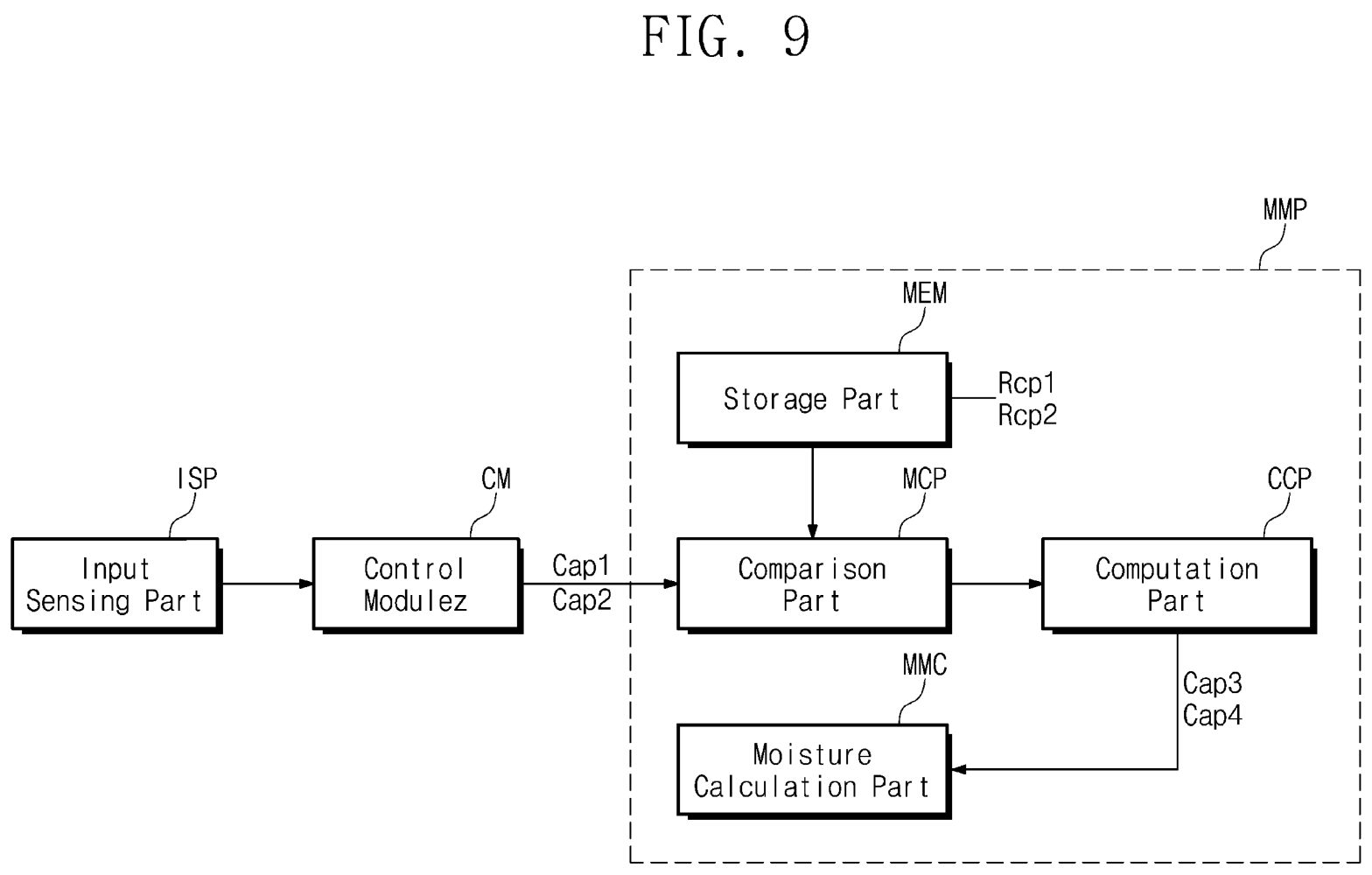

FIG. 9 is a block diagram illustrating a connection relationship between the moisture measurement part shown in FIG. 8 and a configuration around the moisture measurement part according to an embodiment.

Referring to FIG. 9, the display device DD according to an embodiment may include the moisture measurement part MMP. The moisture measurement part MMP may be connected to the control module CM.

The control module CM may control an operating mode of the input sensing part ISP. The input sensing part ISP may be driven in a mutual sensing mode and/or a self-sensing mode by the control module CM. The input sensing part ISP may output a mutual capacitance in the mutual sensing mode. The input sensing part ISP may output a self-capacitance in the self-sensing mode.

The moisture measurement part MMP may include a comparison part MCP, a storage part MEM, a computation part CCP, and a moisture calculation part MMC.

The control module CM may be connected to the comparison part MCP. The control module CM may transmit capacitances Cap1, Cap2 provided from the input sensing part ISP to the comparison part MCP.

The comparison part MCP may receive capacitances Cap1, Cap2 from the control module CM and then may compare the provided capacitances Cap1, Cap2 with reference capacitances Rcp1, Rcp2.

The storage part MEM may store the reference capacitances Rcp1, Rcp2. The storage part MEM may provide the reference capacitances Rcp1, Rcp2 to the comparison part MCP.

The computation part CCP may perform calculations on (or with) the capacitances Cap1, Cap2 provided from the comparison part MCP depending on the comparison result for the capacitances Cap1, Cap2 of the comparison part MCP. The computation part CCP may output the calculated capacitances Cap3, Cap4.

The moisture calculation part MMC may calculate moisture levels corresponding to the calculated capacitances Cap3, Cap4 provided from the computation part CCP. For this operation, the moisture calculation part MMC may include a lookup table. The lookup table may store moisture levels corresponding to various capacitances. The calculated moisture levels may be stored in the lookup table depending on a predetermined moisture calculation relation equation for calculating a relationship between capacitances and moisture levels. Hereinafter, an operation of calculating the user's skin moisture level will be described in more detail.

Figure 10:
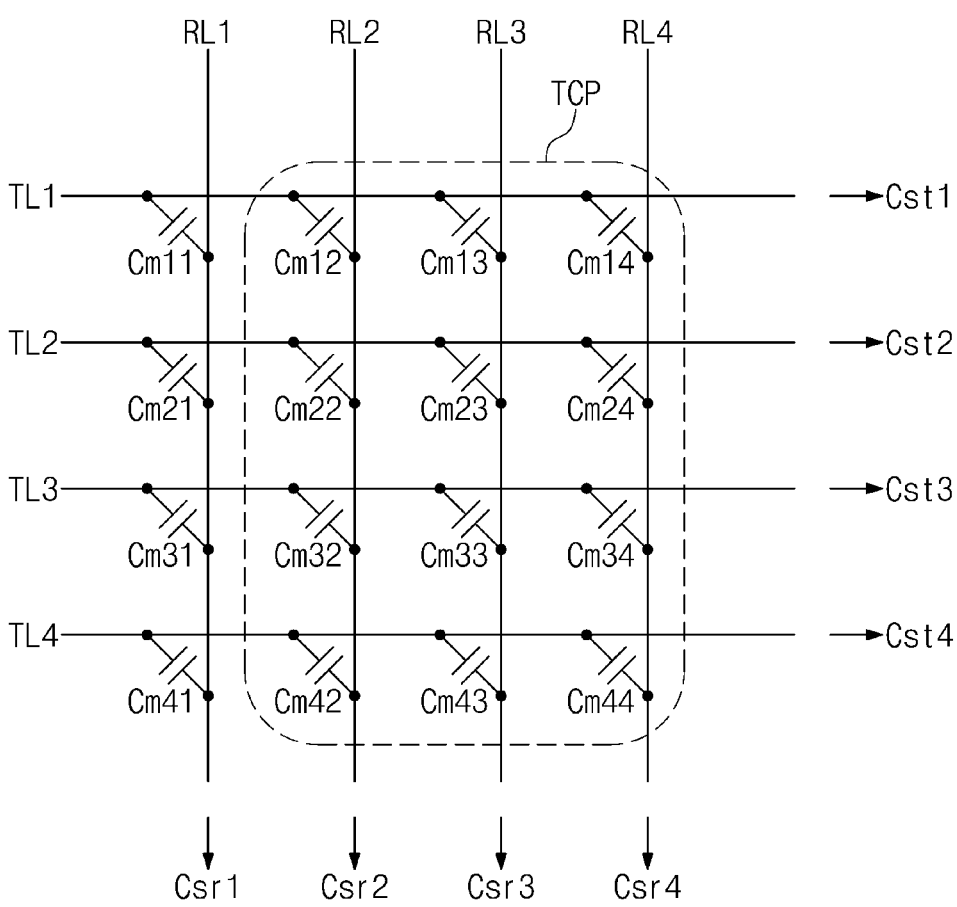
FIG. 10 is a diagram illustrating mutual and self-capacitances of first and second sensing electrodes according to an embodiment.

FIG. 10 is a diagram illustrating mutual and self-capacitances of first and second sensing electrodes according to an embodiment.

Referring to FIG. 10, the first sensing electrodes SE1 (shown in FIG. 5) may include a first transmission sensor part TL1, a second transmission sensor part TL2, a third transmission sensor part TL3, and a fourth transmission sensor part TL4. The second sensing electrodes SE2 (shown in FIG. 5) may include a first reception sensor part RL1, a second reception sensor part RL2, a third reception sensor part RL3, and a fourth reception sensor part RL4.

A 1-1st mutual capacitance Cm11 may be defined between the first transmission sensor part TL1 and the first reception sensor part RL1. A 1-2nd mutual capacitance Cm12 may be defined between the first transmission sensor part TL1 and the second reception sensor part RL2. A 2-1st mutual capacitance Cm21 may be defined between the second transmission sensor part TL2 and the first reception sensor part RL1. Hereinafter, in the same arrangement method, 1-1st to 4-4th mutual capacitances Cm11 to Cm44 may be defined between the first to fourth transmission sensor parts TL1 to TL4 and the first to fourth reception sensor parts RL1 to RL4.

First to fourth transmission self-capacitances Cst1 to Cst4 may be defined in the first to fourth transmission sensor parts TL1 to TL4, respectively. First to fourth reception self-capacitances Csr1 to Csr4 may be defined in the first to fourth reception sensor parts RL1 to RL4, respectively.

A touch area TCP may be defined by a user's touch.

The 1-2nd, 2-2nd, 3-2nd, and 4-2nd mutual capacitances Cm12, Cm22, Cm32, and Cm42 inside the touch area TCP, the 1-3rd, 2-3rd, 3-3rd, and 4-3rd mutual capacitances Cm13, Cm23, Cm33, and Cm43, the 1-4th, 2-4th, 3-4th, and 4-4th mutual capacitances Cm14, Cm24, Cm34, and Cm44, values of the first to fourth transmission self-capacitances Cst1 to Cst4, and values of the second to fourth reception self-capacitances Cst2 to Cst4 may be changed by the user's touch. It may be determined whether the user's touch occurs by detecting the amount of change in a capacitance value.

Figure 11A:
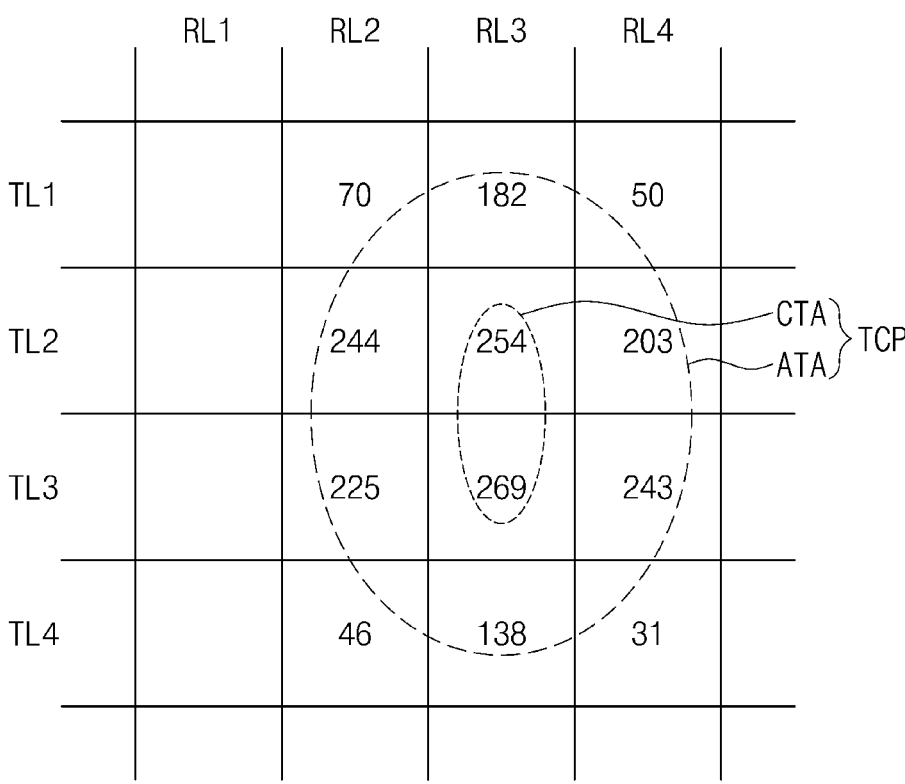
FIG. 11A is a diagram illustrating mutual capacitance values of a touch area in a state where a user employing a display device is grounded according to an embodiment.
Figure 11B:
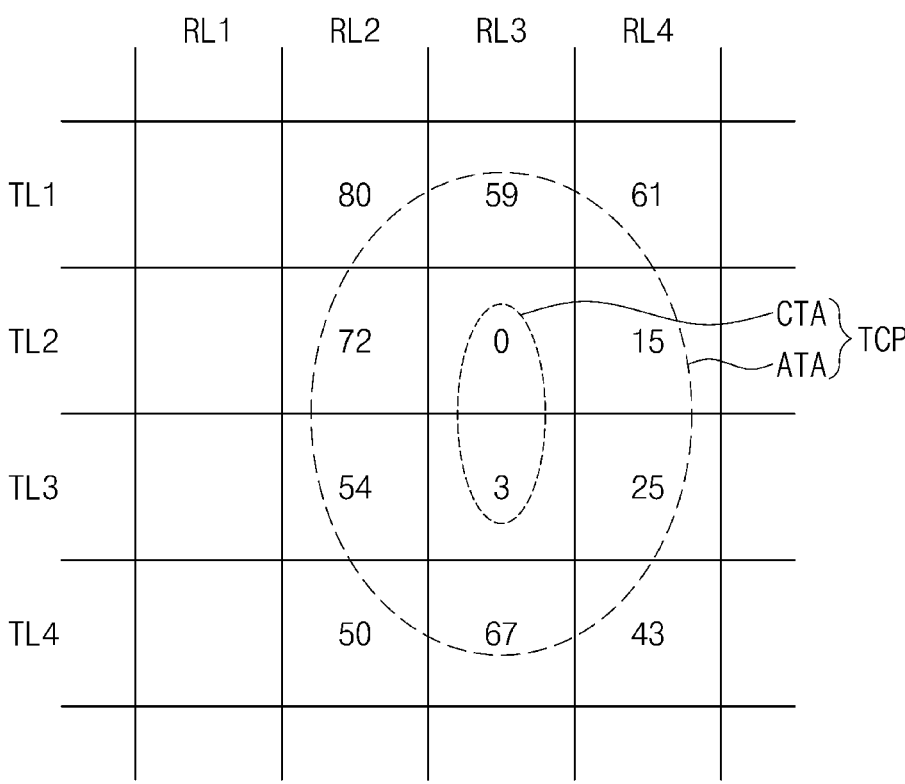
FIG. 11B is a diagram illustrating mutual capacitance values of a touch area in a state where a user employing a display device is not grounded according to an embodiment.

FIG. 11A is a diagram illustrating mutual capacitance values of a touch area in a state where a user employing a display device is grounded according to an embodiment. FIG. 11B is a diagram illustrating mutual capacitance values of a touch area in a state where a user employing a display device is not grounded according to an embodiment.

For convenience of description, FIGS. 11A and 11B illustrate that the 1-1st to 4-4th mutual capacitances Cm11 to Cm44 shown in FIG. 10 are cells defined by the first to fourth transmission sensor parts TL1 to TL4 and the first to fourth reception sensor parts RL1 to RL4.

Referring to FIGS. 11A and 11B, a state where a user employing the display device DD is grounded may be defined as a state where the user touches a ground when the user employs a phone. The ground may serve as an earth.

A state where the user employing the display device DD is not grounded may be defined as a state where the user is separated from a ground when the user employs a phone. For example, because the user is on a bed, the user may be separated from the ground. This state may be defined as a low ground mass (LGM) state. The mutual capacitance detected by the input sensing part ISP may be changed depending on a state where the user is grounded or a state where the user is not grounded on ground.

Referring to FIG. 11A, a central area CTA and a peripheral area ATA around the central area CTA may be defined in the touch area TCP.

The central area CTA may include cells, which are defined in a central portion, from among cells in the touch area TCP. Two cells in the central portion, which are defined by the second and third transmission sensor parts TL2 and TL3 and the third reception sensor parts RL3, are defined as the central area CTA, but are not limited thereto.

The peripheral area ATA may be defined as cells in the touch area TCP other than the central area CTA. The mutual capacitance values of the central area CTA may have 254 and 269. In a state where the user is grounded on the ground, the mutual capacitance values of the peripheral area ATA may be less than the mutual capacitance values of the central area CTA.

Referring to FIG. 11B, in a state where the user is not grounded, the mutual capacitance values of the central area CTA of the touch area TCP may be less than the mutual capacitance values of the peripheral area ATA.

Figure 12:
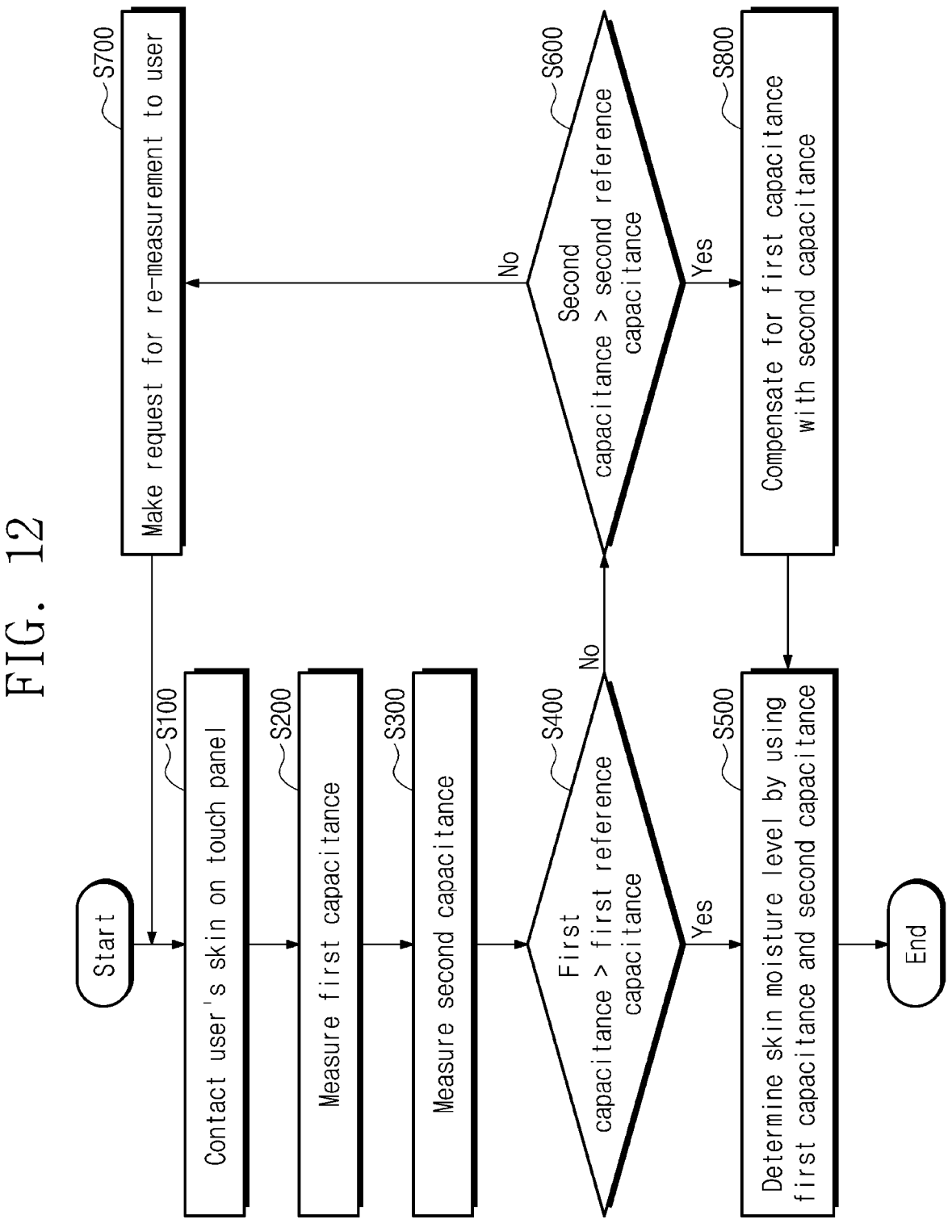
FIG. 12 is a flowchart illustrating a method of measuring skin moisture according to an embodiment.
Figure 13:
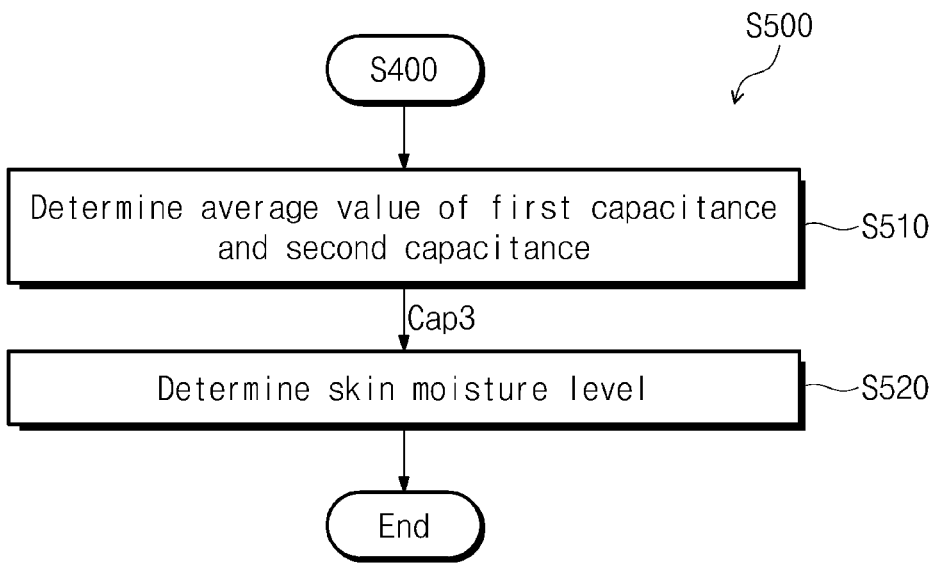
FIG. 13 is a flowchart illustrating a method of determining a skin moisture level using a first capacitance and a second capacitance shown in FIG. 12 according to an embodiment.
Figure 14:
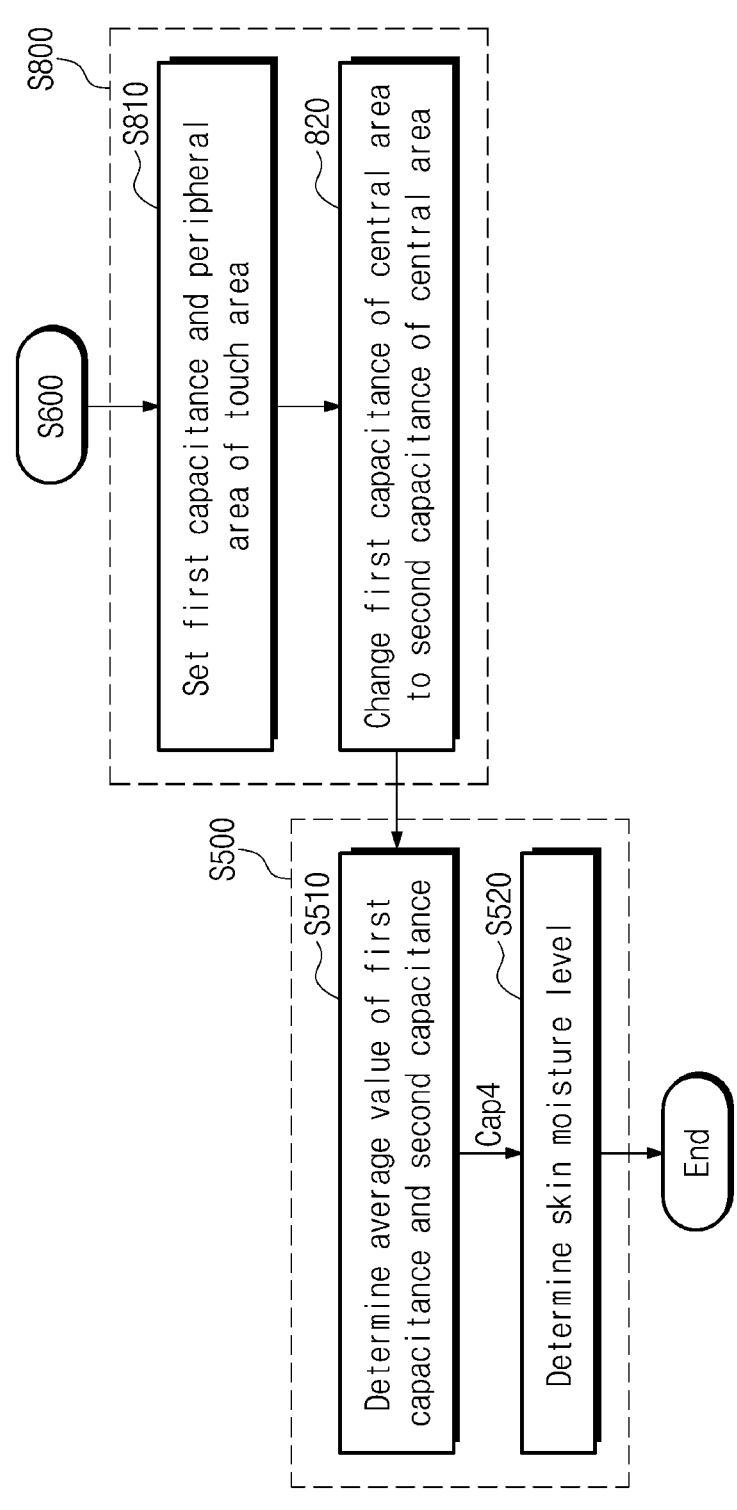
FIG. 14 is a flowchart illustrating a method of compensating for the first capacitance shown in FIG. 12 using the second capacitance according to an embodiment.
Figure 15:
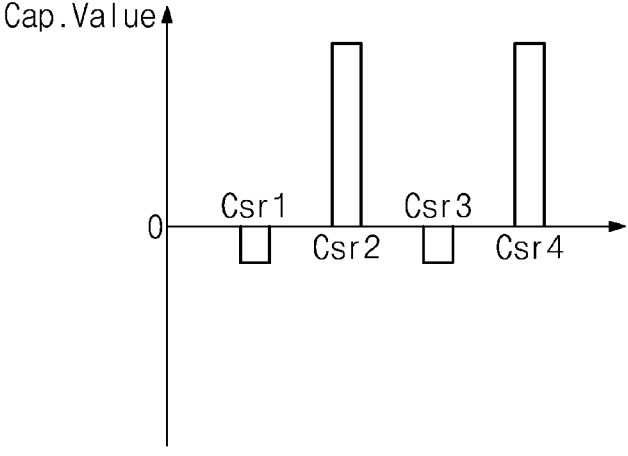
FIG. 15 is a diagram illustrating measurement values of self-capacitances shown in FIG. 10 according to an embodiment.

FIG. 12 is a flowchart illustrating a method of measuring skin moisture according to an embodiment. FIG. 13 is a flowchart illustrating a method of determining a skin moisture level using a first capacitance and a second capacitance shown in FIG. 12 according to an embodiment. FIG. 14 is a flowchart illustrating a method of compensating for the first capacitance shown in FIG. 12 using the second capacitance according to an embodiment. FIG. 15 is a diagram illustrating measurement values of self-capacitances shown in FIG. 10 according to an embodiment.

Hereinafter, FIGS. 9, 11A, and 11B may be referenced together as necessary.

Referring to FIGS. 9, 12, and 13, in a skin moisture measuring method according to an embodiment, in operation S100, a user's skin may contact a touch panel, e.g., may contact window WIN of display device DD. The user's skin in contact with the touch panel may be the user's cheek or forehead, but is not limited thereto.

In operation S200, the first capacitance Cap1 may be measured. The control module CM may drive the input sensing part ISP in a mutual sensing mode. The input sensing part ISP may measure a mutual capacitance in the mutual sensing mode.

A driving signal may be applied to the first sensing electrodes SE1 through the first sensing lines SNL1 of the input sensing part ISP. A sensing signal may be output through the second sensing electrodes SE2 and the second sensing lines SNL2. It may be determined whether the user's touch occurs, or the user's first capacitance Cap1 may be simultaneously measured by sensing the amount of change in mutual capacitance between the first sensing electrodes SE1 and the second sensing electrodes SE2.

In operation S300, the second capacitance Cap2 may be measured. The control module CM may drive the input sensing part ISP in a self-sensing mode. The input sensing part ISP may measure the self-capacitance of a touch area by driving the first sensing electrodes SE1 in the self-sensing mode or driving the second sensing electrodes SE2 in the self-sensing mode.

For example, a driving signal may be applied to the first sensing electrodes SE1 of the input sensing part ISP, and a sensing signal may be output from the first sensing electrodes SE1. Alternatively, a driving signal may be applied to the second sensing electrodes SE2 of the input sensing part ISP, and a sensing signal may be output from the second sensing electrodes SE2. A capacitance component may be not generated between a touch panel and a skin of the user who has touched the touch panel, and the self-capacitance may be increased. Accordingly, the second capacitance Cap2 may be measured.

In operation S400, the comparison part MCP may compare the first capacitance Cap1 and the first reference capacitance Rcp1.

When the first capacitance Cap1 is greater than the first reference capacitance Rcp1, a procedure may proceed to operation S500.

The first capacitance Cap1 may be set to an average value of the mutual capacitances of the central area CTA of the touch area TCP. When a current state is not an LGM state, the first reference capacitance Rcp1 may be set to an average value of mutual capacitance values measured in cells of the touch area TCP. For example, the first reference capacitance Rcp1 may be set to an average value of capacitance values of the touch area TCP shown in FIG. 11A, which indicates that the current state is not the LGM state.

As shown in FIG. 11A, in a state where the user is grounded, the first capacitance Cap1 of the central area CTA may be measured to be greater than the first capacitance Cap1 of the peripheral area ATA. Accordingly, in this case, the first capacitance Cap1 may be greater than the first reference capacitance Rcp1, and it may be determined that the current state is not the LGM state.

As shown in FIG. 11B, in a state where the user is not grounded, the first capacitance Cap1 of the central area CTA of the touch area TCP may be measured to be less than the first capacitance Cap1 of the peripheral area ATA around the central area CTA. As such, in this case, the first capacitance Cap1 may be less than the first reference capacitance Rcp1, and it may be determined that the current state is the LGM state.

In operation S510, an average value of the first capacitance Cap1 and the second capacitance Cap2 may be determined (e.g., calculated). For example, when it is determined by the comparison part MCP that the first capacitance Cap1 is greater than the first reference capacitance Rcp1, the comparison part MCP may transmit the first capacitance Cap1 and the second capacitance Cap2 to the computation part CCP.

The computation part CCP may determine the average value of the first capacitance Cap1 and the second capacitance Cap2, and may output the average value as the third capacitance Cap3. The computation part CCP may transmit the third capacitance Cap3 to the moisture calculation part MMC.

In operation S520, the skin moisture level may be determined. For example, the moisture calculation part MMC may determine and output a moisture value corresponding to the third capacitance Cap3 transmitted from the computation part CCP. The moisture calculation part MMC may output the moisture value, which corresponds to the third capacitance Cap3, from among moisture values stored in a lookup table. The moisture calculation part MMC may transmit the moisture value to the control module CM.

When the first capacitance Cap1 is less than the first reference capacitance Rcp1, a procedure may proceed to operation S600. Compared to the first capacitance Cap1 that is a mutual capacitance, the second capacitance Cap2, which is a self-capacitance, may not be affected by the LGM state where the user is not grounded.

The mutual capacitance varies depending on the LGM state. The moisture level may be normally measured depending on the mutual capacitance measured in a state where the user is grounded. However, in a state where the user is not grounded, the measured mutual capacitance may be changed, and thus, the moisture level may not be measured normally.

The self-capacitance may not be affected by the LGM state. In an embodiment, the first capacitance Cap1 may be compensated using the self-capacitance in the LGM state where the first capacitance Cap1 is less than the first reference capacitance Rcp1.

When the first capacitance Cap1 is less than the first reference capacitance Rcp1, in operation S600, the second capacitance Cap2 may be compared with the second reference capacitance Rcp2.

The second capacitance Cap2 may be set to an average value of the self-capacitances of the central area CTA of the touch area TCP. The second reference capacitance Rcp2 may be set to an average value of self-capacitance values measured in cells of the touch area TCP.

When the second capacitance Cap2 is less than the second reference capacitance Rcp2, the second capacitance Cap2 of the central area CTA of the touch area TCP may be less than the second capacitance Cap2 of the peripheral area ATA.

When the second capacitance Cap2 is less than the second reference capacitance Rcp2, it may be determined that the user's skin is not normally touched in the touch area TCP. FIG. 15 illustrates measurement values of the first to fourth reception self-capacitances Csr1 to Csr4 shown in FIG. 10 according to an embodiment.

As shown in FIG. 15, the third reception self-capacitance Csr3 in the central area CTA of the touch area TCP may be abnormally touched, and thus, may have a negative or zero capacitance value. In addition, the first reception self-capacitance Csr1 outside the touch area TCP, which is not touched by the user, may also have a negative or zero capacitance value. At least because a human skin is curved, the human skin may not uniformly contact the entire touch area TCP.

When the second capacitance Cap2 is less than the second reference capacitance Rcp2, in operation S700, the user may be requested to touch the touch area TCP again. As such, the procedure may proceed to operation S100.

When the second capacitance Cap2 is greater than the second reference capacitance Rcp2, (e.g., in a case of the LGM state), in operation S800, the first capacitance Cap1 may be compensated with the second capacitance Cap2. Even in the LGM state, the accuracy of a skin moisture level measurement value may be improved by compensating for the first capacitance Cap1, which is not normally measured, with the second capacitance Cap2, which may be measured regardless of the LGM state.

In operation S810, the central area CTA of the touch area TCP and the peripheral area ATA around the central area CTA may be set. The central area CTA and the peripheral area ATA may be the same as the central area CTA and the peripheral area ATA in operation S400.

When the user's skin is abnormally touched on a touch panel, the second capacitance Cap2 of the central area CTA may be measured to be less than the second capacitance Cap2 of the peripheral area ATA. At this time, the second capacitance Cap2 of the central area CTA may be measured to be less than the second capacitance Cap2 at a point in time when the user's skin is normally touched by the touch panel.

When the first capacitance Cap1 is less than the first reference capacitance Rcp1, and the second capacitance Cap2 is greater than the second reference capacitance Rcp2, it may be determined that a current state is the LGM state. In operation S820, the first capacitance Cap1 of the central area CTA may be changed to the second capacitance Cap2 of the central area CTA and then may be compensated. The computation part CCP may compensate for the first capacitance Cap1 of the central area CTA with the second capacitance Cap2 of the central area CTA.

In operation S510, an average value of the compensated first capacitance Cap1 and the second capacitance Cap2 may be determined. The computation part CCP may output the average value of the compensated first capacitance Cap1 and the second capacitance Cap2 as a fourth capacitance Cap4. The computation part CCP may transmit the fourth capacitance Cap4 to the moisture calculation part MMC.

In operation S520, the moisture calculation part MMC may calculate the fourth capacitance Cap4 transmitted from the computation part CCP as the corresponding moisture value in a lookup table. In some embodiments, the moisture calculation part MMC may transmit the calculated moisture value to the display module DM. The moisture value may be displayed in the display module DM and may be provided to the user.

Figure 16:
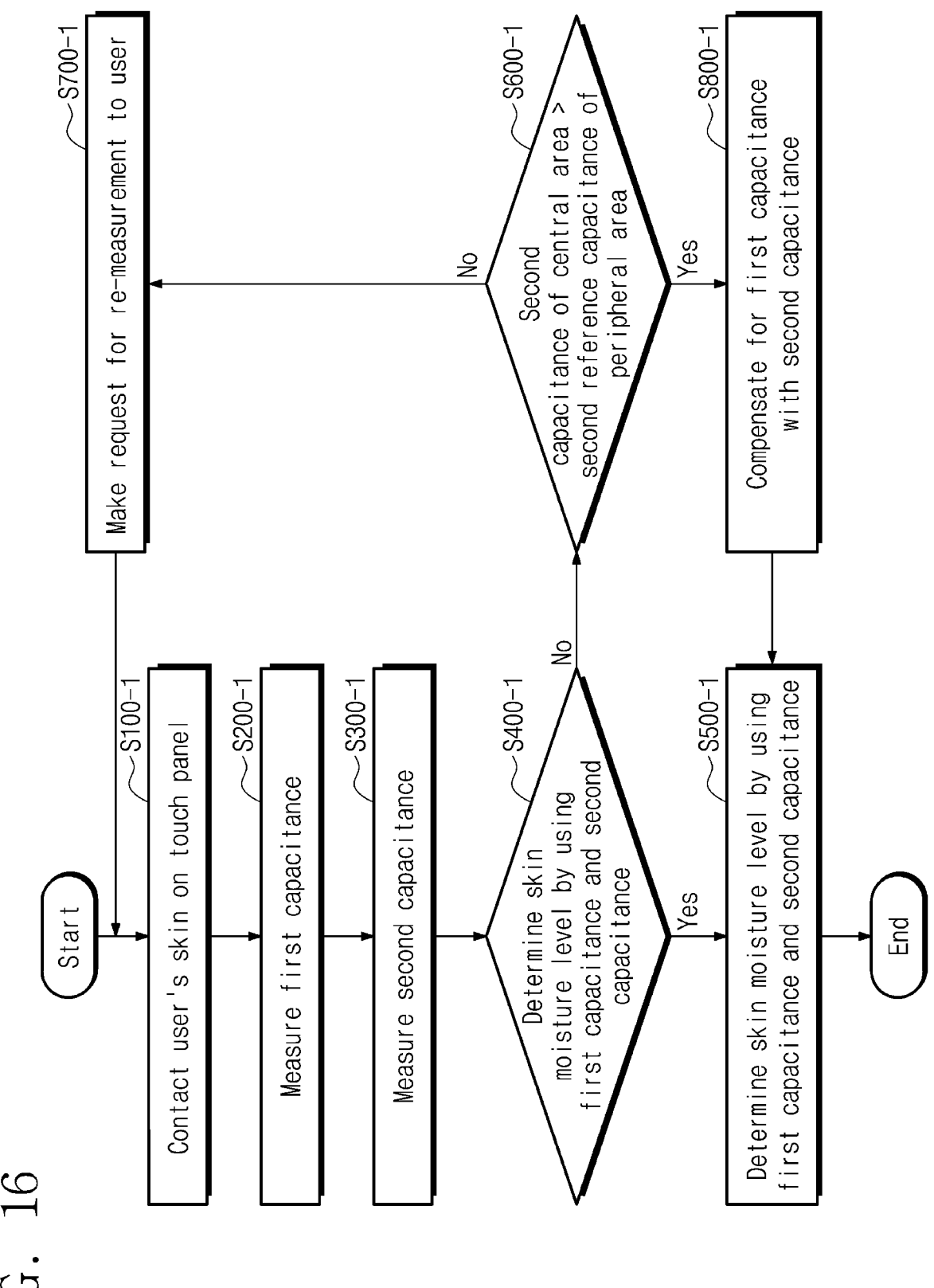
FIG. 16 is a flowchart illustrating a method of measuring skin moisture according to an embodiment.

FIG. 16 is a flowchart illustrating a method of measuring skin moisture according to an embodiment.

For convenience of description, the description of the same configuration as the skin moisture measurement method will be omitted to avoid redundancy.

Referring to FIGS. 11A, 111B, 15, and 16, in operation S400-1, the first capacitance Cap1 of the central area CTA and the first reference capacitance Rcp1 of the peripheral area ATA may be compared.

The first capacitance Cap1 may be set as an average value of the capacitance values of the central area CTA. The first reference capacitance Rcp1 may be set as an average value of capacitance values of the peripheral area ATA.

When the first capacitance Cap1 of the central area CTA is less than the first reference capacitance Rcp1 of the peripheral area ATA, the second capacitance Cap2 of the central area CTA may be compared with the second reference capacitance Rcp2 of the peripheral area ATA.

The second capacitance Cap2 may be set to an average value of the capacitance values of the central area CTA. The second reference capacitance Rcp2 may be set to 30% of the average value of the capacitance values of the peripheral area ATA.

When the second capacitance Cap2 is less than the second reference capacitance Rcp2, it is determined that a user's skin is abnormally touched on a touch panel. In operation S700-1, the user may be requested to measure a skin moisture level again.

When the second capacitance Cap2 is greater than the second reference capacitance Rcp2, it may be determined that a current state is an LGM state. In operation S800-1, the first capacitance Cap1 may be compensated with the second capacitance Cap2, and thus, the user's skin moisture level may be determined with the compensated capacitance value.

According to various embodiments, it is possible to determine an LGM state of a mutual capacitance, and to compensate for a capacitance value even in the LGM state. As such, the accuracy of a skin moisture level measurement value may be improved.

Although certain embodiments and implementations have been described herein, other embodiments and modifications will be apparent from this description. Accordingly, the inventive concepts are not limited to such embodiments, but rather to the broader scope of the accompanying claims and various obvious modifications and equivalent arrangements as would be apparent to one of ordinary skill in the art.

What is claimed is:

1. A method of measuring skin moisture, the method comprising:

measuring, in response to a touch on a touch panel, a first capacitance of a touch area by driving a first electrode and a second electrode of the touch panel in a mutual sensing mode, the first electrode comprising a plurality of transmission sensor parts, the second electrode comprising a plurality of reception sensor parts, the transmission sensor parts and the reception sensor parts forming a mesh;

measuring, in response to the touch on the touch panel, a second capacitance of the touch area driving one electrode of the first electrode and the second electrode in a self-sensing mode;

comparing the first capacitance with a first reference capacitance;

determining, in response to the first capacitance being greater than the first reference capacitance, a skin moisture level using the first capacitance and the second capacitance;

comparing, in response to the first capacitance being less than the first reference capacitance, the second capacitance with a second reference capacitance;

compensating, in response to the second capacitance being greater than the second reference capacitance, the first capacitance using the second capacitance, and determining the skin moisture level using the compensated first capacitance;

determining, in response to the second capacitance being less than the second reference capacitance, the user's skin is not normally touched in the touch area, wherein the compensating of the first capacitance with the second capacitance comprises:

setting the touch area to include a central area and a peripheral area around the central area, the central area being defined by a first group of the transmission sensor parts and the reception sensor parts and forming a first central capacitance and a second central capacitance, the peripheral area being defined by a second group of the transmission sensor parts and the reception sensor parts and forming a first peripheral capacitance and a second peripheral capacitance; and compensating the first central capacitance with the second central capacitance.

2. The method of claim 1, wherein the determining of the skin moisture level using the first capacitance and the second capacitance comprises:

generating a third capacitance by determining an average value of the first capacitance of the touch area and the second capacitance of the touch area; and determining the skin moisture level using the third capacitance.

3. The method of claim 2, wherein the determining of the skin moisture level using the first capacitance and the second capacitance further comprises:

determining a moisture value, which corresponds to the third capacitance, from among moisture values stored in a lookup table, the moisture value being the skin moisture level.

4. The method of claim 1, further comprising:

outputting an average value of the compensated first capacitance of the touch area and the second capacitance of the touch area as a fourth capacitance; and determining a moisture value, which corresponds to the fourth capacitance, from among moisture values stored in a lookup table, the moisture value being the skin moisture level.

5. The method of claim 1, wherein:

the first capacitance of the touch area is less than the first reference capacitance; and the first central capacitance is less than the first peripheral capacitance.

6. The method of claim 5, wherein, in a state where a user performing the touch is not grounded, the first central capacitance is determined to be less than the first peripheral capacitance.

7. The method of claim 6, wherein, in a state where the user performing the touch is grounded, the first reference capacitance is set to an average value of the touch area capacitances.

8. The method of claim 1, wherein, in response to the second capacitance of the touch area being less than the second reference capacitance, the second central capacitance is less than the second peripheral capacitance.

9. The method of claim 8, wherein, in response to the determining the user's skin is not normally touched in the touch area, the touch panel is in an abnormal touch state, and the second central capacitance in the abnormal touch state is less than a second central capacitance in a normal touch state.

10. The method of claim 9, wherein:

the second central capacitance is an average value of capacitances measured in cells in the central area; and the second reference capacitance is set to 30% of an average value of the second peripheral capacitances.

11. The method of claim 1, further comprising:

requesting, in response to the second capacitance of the touch area being less than the second reference capacitance, another touch of the touch panel.

12. The method of claim 1, wherein, in the mutual sensing mode, a driving signal is applied to the first electrode and a sensing signal is output through the second electrode.

13. The method of claim 1, wherein, in the self-sensing mode, a driving signal is applied to the one electrode of the first electrode and the second electrode, and a sensing signal is output from the one electrode.

* * * * *